(12) United States Patent
Okada et al.

(10) Patent No.: US 7,772,336 B2
(45) Date of Patent: Aug. 10, 2010

(54) METHOD FOR PRODUCING α-METHYLSTYRENE AND HEAT-RESISTANT STYRENE-BASED COPOLYMER USING THE α-METHYLSTYRENE

(75) Inventors: Yuji Okada, Tokyo (JP); Kenji Ebara, Tokyo (JP)

(73) Assignee: Asahi Kasei Chemicals Corporation, Tokyo (JP)

( * ) Notice: Subject to any disclaimer, the term of this patent is extended or adjusted under 35 U.S.C. 154(b) by 80 days.

(21) Appl. No.: 12/226,224

(22) PCT Filed: Apr. 16, 2007

(86) PCT No.: PCT/JP2007/058262

§ 371 (c)(1),
(2), (4) Date: Oct. 10, 2008

(87) PCT Pub. No.: WO2007/119849

PCT Pub. Date: Oct. 25, 2007

(65) Prior Publication Data

US 2009/0171053 A1    Jul. 2, 2009

(30) Foreign Application Priority Data

Apr. 17, 2006 (JP) .............................. 2006-113271
Apr. 18, 2006 (JP) .............................. 2006-114013
May 24, 2006 (JP) .............................. 2006-143707

(51) Int. Cl.
C08F 2/00 (2006.01)
C07C 7/148 (2006.01)
C07C 7/173 (2006.01)
C08F 212/08 (2006.01)

(52) U.S. Cl. .................... 526/77; 526/173; 526/347; 585/853; 585/854; 585/855

(58) Field of Classification Search .................. 526/77, 526/173, 347; 585/853, 854, 855
See application file for complete search history.

(56) References Cited

U.S. PATENT DOCUMENTS

| 4,125,568 | A | * | 11/1978 | Theriot et al. ............... 585/834 |
| 4,200,713 | A | | 4/1980 | Wingler et al. |
| 4,647,632 | A | | 3/1987 | Priddy |
| 5,089,572 | A | * | 2/1992 | Marchand et al. ............. 526/77 |
| 2003/0008952 | A1 | | 1/2003 | Kawasaki |
| 2007/0083024 | A1 | | 4/2007 | Ebara |

FOREIGN PATENT DOCUMENTS

| JP | 53-137290 A | 11/1978 |
| JP | 55-094326 A | 7/1980 |
| JP | 58-189209 A | 11/1983 |
| JP | 63-077908 A | 4/1988 |
| JP | 64-007058 A | 2/1989 |
| JP | 03-036043 B | 2/1991 |
| JP | 03-258733 A | 11/1991 |
| JP | 05-255450 A | 10/1993 |
| JP | 2000-072992 | 3/2000 |
| JP | 2000-086559 A | 3/2000 |
| JP | 2002-121344 A | 4/2002 |
| JP | 2004-315827 A | 11/2004 |
| JP | 2006-052346 A | 2/2006 |
| WO | WO-2005/044864 | 5/2005 |
| WO | WO-2005/070978 A1 | 8/2005 |

OTHER PUBLICATIONS

Journal of Applied Polyme Science, vol. 41, p. 383-390 (1990).
R.H. Boundry, R.F. Boyer, Styrene, its Polymers, Copolymers and Derivatives, Reinhold (1952).
Journal of Applied Polymer Science, vol. 40, p. 41-45 (1990).

* cited by examiner

*Primary Examiner*—Fred M Teskin
(74) *Attorney, Agent, or Firm*—Morgan Lewis & Bockius LLP

(57) ABSTRACT

An object of the present invention is to provide highly pure α-methylstyrene by efficiently removing polar substances present in the α-methylstyrene. The present invention discloses a method for purifying α-methylstyrene by reacting polar substances contained in the α-methylstyrene in the presence of a basic substance, and separating a reaction product of the polar substance and the α-methylstyrene.

10 Claims, No Drawings

METHOD FOR PRODUCING α-METHYLSTYRENE AND HEAT-RESISTANT STYRENE-BASED COPOLYMER USING THE α-METHYLSTYRENE

TECHNICAL FIELD

The present invention relates to a method for obtaining highly pure α-methylstyrene as a polymerization monomer. More particularly, the present invention relates a method for purifying α-methylstyrene to a high purity by removing polar substances, such as aldehydes and ketones, contained in trace amounts in α-methylstyrene by reaction in the presence of a basic substance, whereby efficient removal can be achieved without requiring a complex process. Moreover, the present invention relates to a styrene-based copolymer having little coloring, and superior heat resistance, weather resistance, melt stability, moldability, strength and rigidity able to be obtained by using this monomer.

BACKGROUND ART

Styrene-based resins are used in an extremely wide range of applications as a result of not only having superior material performance in terms of transparency, rigidity, dimensional stability and the like, but also as a result of being able to be processed in various forms such as rolled sheets, films, foamed sheets, foamed boards and blow molded articles, and because many styrene-based resins can be produced inexpensively and in large volume by bulk polymerization using radical polymerization, solution polymerization using a high monomer concentration, suspension polymerization or emulsion polymerization.

Although typical examples of styrene-based resins may include polystyrene (GPPS), styrene/acrylonitrile (AS), styrene/methyl methacrylate (MS), styrene/methacrylic acid (SMM), styrene/maleic anhydride (SMA) and the like, styrene homopolymers (polystyrene (GPPS)) is used the most universally.

Polystyrene has numerous superior properties, and because it is inexpensive, has high usage value and is used in various applications. Some major applications thereof are indicated below.

(Packaging Applications)

Lunchbox containers (foamed sheet: PSP), cup noodle containers (foamed sheet: PSP), clear cups, spoons, forks, vegetable packaging sheets (biaxially oriented sheets), envelop windows (Home Appliance Applications)

Television, air-conditioner and OA equipment packaging, electric refrigerator trays, cassette, MD and MO shells (Miscellaneous Household Goods)

Toys, stationary articles (Building Material Applications)

Insulation (foamed boards), tatami mats (foamed boards)

However, there were some applications that were unable to be satisfied even by the performance of this resin, such as applications that prevented this resin from being used due to insufficient heat resistance. More specifically, since the GPPS heat resistance is about 100° C. (glass transition temperature), in applications involving contact with hot steam for disinfection by boiling, food packaging applications requiring heating in a microwave oven or applications involving molded automotive parts susceptible to exposure to high temperatures in the summer, this resin was unable to be used without risk of causing deformation to the molded articles.

One way of enhancing the heat resistance of polystyrene may include copolymerizing styrene with a monomer containing a polar functional group, examples of which may include copolymers of styrene and methacrylic acid (SMAA), copolymers of styrene and maleic anhydride (SMA) and copolymers of styrene and maleimide anhydride (SMA). Heat resistance can be arbitrarily changed by controlling the amount of monomer containing the polar functional group in the copolymer composition. For example, a typical example of a heat-resistant styrene-based resin in the form of SMAA has a Vicat heat resistance temperature of from 105 to 125° C. However, when polymers having the polar functional group are exposed to high temperatures, a crosslinking reaction of the polymer chain occurs due to side reactions of the polar groups, and as a result, gel-like substances are formed that cause a decrease in molding processability due to increased viscosity, thereby preventing these polymers from being adequately accepted by users from the viewpoints of quality and productivity.

In addition, increased susceptible to the occurrence of crosslinking reactions under conditions of high-temperature melt retention means increased susceptibility of high molecular weight polymers to deformation during molding processing, thereby making it difficult to recycle and reuse resins. For example, when obtaining an injection molded article, end materials (skeletons) are generated during formation of sprue and runner components and when obtaining molded articles from biaxially oriented sheets or foamed sheets. These are usually reused by partially mixing with virgin pellets after being crushed or cut up, or are typically reused by partially mixing into general-purpose resins such as polystyrene.

However, reuse become difficult if the flow properties of a resin change due to crosslinking of high molecular weight polymers during melt processing, and there was the problem of limitations being placed on the use of these resins for recycling to virgin pellets. Moreover, copolymers containing the polar functional group typically have poor compatibility with polystyrene and even if mixed by melting, not only do they lead to a decrease in mechanical properties, but also cause a loss of transparency, thereby preventing these copolymers from being recycled to general-purpose polystyrene.

With the increasing emphasis being placed on effective utilization of resins in recent years, various types of recycling methods have been developed and implemented. Being able to recycle, rework and reuse resins is an essential requirement on the resin markets of the future. Resin materials developed in the future will be required to be resins able to be effectively recycled without undergoing hardly any decrease in molecular weight or generation of monomers due to severing of the polymer chain even if going through several rounds of melt processing. Thus, there is a desire for the development of resin materials exhibiting higher melt stability than conventional styrene-based copolymers.

Another problem of conventional heat-resistant styrene-based resins was the narrow range of processing conditions during molding. Improving the heat resistance of a copolymer is equivalent to improving the temperature at which flow of the polymer chain begins. Thus, if it is desired to obtain flow properties similar to those of polystyrene during molding processing, it is necessary to raise the processing temperature corresponding to an improvement in heat resistance. However, in the case of styrene-based copolymers containing the polar functional group, the decomposition starting temperature does not improve corresponding to heat resistance. Consequently, the molding processing temperature range becomes narrow and as a result, there were problems in terms of leading to decreases in productivity and quality.

There are also methods for improving the heat resistance of styrene-based resins by using a monomer that does not contain the polar functional group. For example, a copolymer of styrene and α-methylstyrene is known to demonstrate an increase in the glass transition temperature as the content of α-methylstyrene increases (see, for example, Non-Patent Document 1).

However, in the case of attempting to copolymerize styrene and α-methylstyrene using a typical example of an industrial production process in the form of radical solution polymerization, none of these methods have been able to be used industrially due to numerous problems as indicated below:

1) high molecular weight polymerization is difficult due to the low ceiling temperature of α-methylstyrene of about 60° C.;
2) target heat resistance cannot be obtained due to limitations on the content of α-methylstyrene in the copolymer; and
3) thermal decomposition of the copolymer occurs easily depending on molding processing conditions due to poor thermal stability during melting, thereby resulting in the generation of monomer components and susceptibility to decreases in molecular weight.

On the other hand, since α-methylstyrene can undergo living anionic polymerization by using a butyl lithium initiator, copolymers of styrene and α-methylstyrene can be also be produced by living anionic polymerization (see, for example, Patent Document 1).

Therefore, a method has been proposed for solving the problems of radical solution polymerization by carrying out living anionic polymerization according to a continuous living polymerization method using a complete mixing type of polymerization reactor (see, for example, Patent Document 2). This method is characterized by carrying out polymerization using a continuous type of complete mixing reactor such that the concentrations of α-methylstyrene monomer, styrene monomer and living copolymer present in the living polymerization reaction system remain constant at all times, and offers the following effects:

1) high molecular polymerization is possible due to the use of a living polymerization method;
2) the content of α-methylstyrene in the copolymer can be controlled since the concentration in the reaction system can be kept constant; and,
3) thermal stability during melting improves due to the absence of head-to-head bonds, tail-to-tail bonds and other unstable bonds in the main chain of copolymer due to the use of anionic polymerization.

However, living anionic polymerization is typically susceptible to the effects of impurities contained in the raw materials. In particular, active anions are known to easily react with polar substances such as water, aldehydes, ketones and alcohols. If polar substances are present, even in trace amounts, in an anionic polymerization reaction system, the active anions react with the polar substances resulting in the formation of stable bonds, thereby causing the problem of interrupting polymerization. Consequently, when carrying out living anionic polymerization, polar substances in raw materials must be reduced, and entrance of polar substances into the reaction system must be suppressed as much as possible.

In addition, the above-mentioned polar substances and reaction products of active anions and polar substances undergo degeneration during the course of the polymerization process resulting in the possibility of the formation of colored substances. In this case, this can result in coloring of the polymer or decreases in polymer physical properties, thereby making this undesirable. From this viewpoint as well, polar substances in the raw materials are preferably eliminated as much as possible.

However, the typical process for industrial production of α-methylstyrene is the cumene-phenol production process. This cumene-phenol production process contains a step in which cumene hydroperoxide obtained by oxidation of raw material cumene is concentrated to 80 to 85% followed by acid decomposition to phenol and acetone and neutralization/washing. The resulting crude phenol contains such substances as acetone, water, cumene, α-methylstyrene and phenol, and purified phenol is produced from this crude phenol by distillation, while at the same time, acetone and α-methylstyrene are respectively separated and recovered (see, for example, Patent Documents 3 and 4).

However, in the case of attempting to respectively separate and recover acetone and α-methylstyrene simultaneous to production of purified phenol using the process described above, the following problems occur. Namely, substances having a boiling point close to that of α-methylstyrene for which separation is difficult by distillation are present among the polar substances such as aldehydes and ketones produced as by-products during phenol production. Thus, polar substances end up contaminating the α-methylstyrene in the form of impurities in the case of distillative purification alone.

In addition, a method is carried out for the purpose of removing impurities containing polar substances comprises supplying crude α-methylstyrene to an alkaline washing tank prior to distillation and washing in the tank followed by supplying to a distillation column to recover the product α-methylstyrene (see, for example, Patent Documents 5 and 6). However, in the case of washing in an alkaline washing tank according to the above method, since the solubility of polar substances in alkaline solution is inadequate, the polar substances end up remaining in the α-methylstyrene, thereby preventing the removal of trace amounts of polar substances. In addition, although methods have also been considered involving reacting polar substances in an alkaline washing tank to obtain lowly volatile substances and increasing the difference in relative volatility between these substances and α-methylstyrene followed by distillation, in this case, polar substances cannot be removed unless the reaction is allowed to proceed to nearly 100%.

On the other hand, an example of a typical method for purifying polymerization monomers in the form of styrenes in the laboratory may include washing with an alkaline substance such as an aqueous sodium thiosulfate solution or aqueous sodium hydroxide solution and water followed by drying and distillation (see, for example, Non-Patent Document 2). However, although the above method makes it possible to eliminate the use of a polymerization inhibitor, peroxide and polymer, polar substances cannot be completely removed from α-methylstyrene for the same reasons as in the case of washing in an alkaline washing tank as described above.

In addition, although a method has indicated including adding alkyl lithium and the like to monomers prior to polymerization to deactivate polar substances followed by distillation, in this case, since considerable amounts of polymers, oligomers and the like are formed accompanying the reaction, this method is not considered to be industrially suitable. In addition, the monomers may become contaminated with oligomers depending on the distillation conditions, thereby having the potential for having a detrimental effect on polymerization.

Another example of a method for purifying α-methylstyrene may include purification using a column packed with silica gel, alumina or ion exchange resin and the like (see, for example, Patent Document 2 and Non-Patent Document 3). However, these packing materials usually contain acidic or basic components. Namely, in the above method, there is a possibility of an acidic component present in the packing material causing the formation of low molecular weight oligomers of α-methylstyrene, or a basic component present in the packing material causing deterioration of polar substances to high molecular weight condensates. The formed oligomers or high molecular weight condensates contaminate the monomers in the column, and if polymerization is carried out using these contaminated monomers, there is a risk of polymerization being interrupted or the reaction being impaired in other ways. Moreover, since these oligomers and high molecular weight condensates have low volatility, they are unable to be removed from the polymerized polymer solution, and end up contaminating the final product polymer. As a result, problems occur leading to deterioration of polymer performance in the form of a decrease in the heat resistance of the product polymer or yellowing.

As has been described above, none of the methods of the prior art are able to be effectively used industrially as a method for purifying α-methylstyrene.

Patent Document 1: Japanese Patent Publication No. H6-10219

Patent Document 2: Japanese Patent Application Laid-open No. 2006-052346

Patent Document 3: Japanese Patent Application Laid-open No. S55-94326

Patent Document 4: Japanese Patent Publication No. S64-7058

Patent Document 5: Japanese Patent Application Laid-open No. 2000-86559

Patent Document 6: Japanese Patent Application Laid-open No. H3-258733

Non-Patent Document 1: Journal of Applied Polymer Science, Vol. 41, p. 383 (1990)

Non-Patent Document 2: R. H. Boundry, R. F. Boyer, "Styrene, its Polymers, Copolymers and Derivatives", Reinhold (1952)

Non-Patent Document 3: Journal of Applied Polymer Science, Vol. 40, p:41 (1990)

DISCLOSURE OF THE INVENTION

Problems to be Solved by the Invention

An object of the present invention is to provide a method for purifying α-methylstyrene allowing the obtaining of highly pure α-methylstyrene containing hardly any polar substances by efficiently removing polar substances contained in trace amounts in α-methylstyrene in a method for purifying α-methylstyrene. Moreover, an object of the present invention is to provide a copolymer containing a styrene-based copolymer that improves heat resistance and weather resistance, which were the disadvantages of SMAA and SMA, and also has superior melt stability, moldability, strength, rigidity and recyclability while preventing polymer coloring and retaining the superior properties of conventional styrene-based resins in the form of transparency, dimensional stability and molding processability, by using this α-methylstyrene.

Means for Solving the Problems

As a result of conductive extensive studies to solve the above-mentioned problems, the inventors of the present invention found that specific polar substances contained in trace amounts in α-methylstyrene cause polymer coloring and impaired control of polymerization, and that oligomers formed in conventional purification methods also cause polymer coloring and decreases in physical properties. In order to eliminate these problems, the inventors of the present invention found that a method for purifying α-methylstyrene is able to efficiently remove polar substances without forming oligomers by employing a method for removing these polar substances so as to control the content of polar substances and oligomers within a fixed range by reacting polar substances contained in α-methylstyrene in the presence of a basic substance and then separating low boiling point by-products formed by this reaction from reaction products of the polar substances, thereby leading to completion of the present invention.

Namely, the present invention is as described below, and provides a method for purifying α-methylstyrene, α-methylstyrene for living anionic polymerization, and a styrene-based copolymer.

In a first aspect, the present invention provides:

[1] a method for purifying α-methylstyrene, comprising the steps of:

reacting a polar substance contained in α-methylstyrene in the presence of a basic substance; and separating a reaction product of the polar substance and the α-methylstyrene.

[2] the method for purifying α-methylstyrene according to item [1], comprising the steps of:

reacting the polar substance contained in the α-methylstyrene in the presence of a basic substance; and separating a low boiling point component produced by the reaction, the α-methylstyrene and a reaction product of the polar substance.

[3] the method for purifying α-methylstyrene according to item [1] or [2], comprising the steps of:

1) reacting a polar substance contained in the α-methylstyrene in the presence of a basic substance;

2) separating a low boiling point component produced by the reaction from a mixture of a reaction product of the polar substance and the α-methylstyrene; and 3) separating α-methylstyrene from the mixture of the reaction product of the polar substance and the α-methylstyrene.

[4] the method for purifying α-methylstyrene according to item [1] or [2], comprising the steps of:

1) reacting a polar substance contained in the α-methylstyrene in the presence of a basic substance;

2) separating a mixture of a low boiling point component produced by the reaction and the α-methylstyrene from the reaction product of the polar substance; and 3) separating the α-methylstyrene from the mixture of the low boiling point component produced by the reaction and the α-methylstyrene.

[5] the method for purifying according to any one of items [1] to [4], wherein the polar substance contains a carbonyl group-containing compound.

[6] the method for purifying according to any one of items [1] to [5], wherein the polar substance contains a carbonyl group-containing compound and a mixture of phenol and catechol.

[7] the method for purifying according to item [5] or [6], wherein the carbonyl group-containing compound is a compound represented by the following general formula (1) or general formula (2):

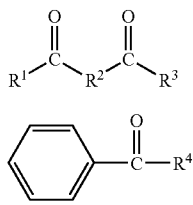

(wherein each of $R^1$, $R^3$ and $R^4$ independently represents a hydrogen atom or an alkyl group having 1 to 6 carbon atoms, and $R^2$ represents an alkyl group having 1 to 6 carbon atoms).

[8] the method for purifying according to item [7], wherein the carbonyl group-containing compound contains at least one compound selected from acetonylacetone, 3-methyl-2-cyclopetenone, benzaldehyde and acetophenone.

[9] the method for purifying according to any one of items [1] to [8], wherein a basicity of the basic substance is 10 or more in terms of the acid dissociation constant pKa of a conjugate acid of the basic substance.

[10] the method for purifying according to item [9], wherein the basic substance is a basic compound containing an alkaline metal or alkaline earth metal.

In a second aspect, the present invention also provides:

[11] an α-methylstyrene for anionic polymerization, wherein a total of an aliphatic carbonyl compound represented by the following general formula (1) and an intramolecular dehydration condensate thereof is 100 ppm by weight or less, and an aromatic carbonyl compound represented by the following general formula (2) is present at 30 ppm by weight or less:

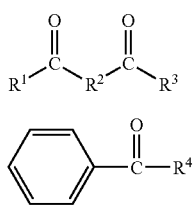

(wherein each of $R^1$, $R^3$ and $R^4$ independently represents a hydrogen atom or an alkyl group having 1 to 6 carbon atoms, and $R^2$ represents an alkyl group having 1 to 6 carbon atoms).

[12] the 0-methylstyrene for anionic polymerization according to item [11], wherein a content of alcohol, phenol and catechols is 10 ppm by weight or less.

[13] the α-methylstyrene for anionic polymerization according to item [11] or [12], wherein a α-methylstyrene dimer is less than 5 ppm.

[14] the α-methylstyrene for anionic polymerization according to any one of items [11] to [13], wherein a content of benzofuran is from 5 to 5000 ppm by weight.

In a third aspect, the present invention further provides:

[15] a styrene-based copolymer obtained by copolymerizing the α-methylstyrene according to any one of claims 11 to 14 and a vinyl aromatic monomer represented by the following general formula (3) using anionic polymerization:

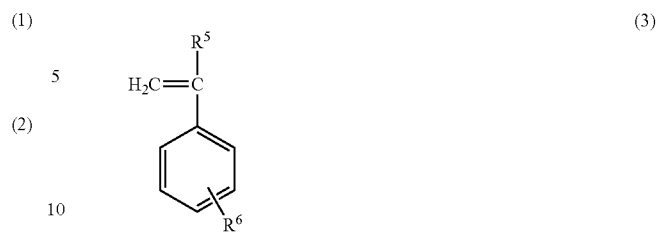

(wherein $R^5$ represents a hydrogen atom, an alkyl group having 2 or more carbon atoms or a phenyl group, and $R^6$ represents a hydrogen atom, a halogen, a hydroxyl group, an alkyl group, an alkoxy group, a carboxyl group or a haloalkyl group).

[16] the styrene-based copolymer according to item [15], wherein a yellow index value is 3 or less.

ADVANTAGEOUS EFFECTS OF THE INVENTION

The present invention is useful as a method for obtaining a highly pure α-methylstyrene for anionic polymerization without requiring a complex process capable of removing by distillation trace amounts of polar substances, generally unable to be removed by distillation, by efficiently modifying to high molecular weight condensates by reacting a polar substance in α-methylstyrene in the presence of a basic substance and separating from low boiling point reaction by-products. In addition, use of an α-methylstyrene purified by the purification method of the present invention makes it possible to obtain a copolymer containing a styrene-based copolymer that improves heat resistance and weather resistance, which were the disadvantages of SMM and SMA, and also has superior melt stability, moldability, strength, rigidity and recyclability while preventing polymer coloring and retaining the superior properties of conventional styrene-based resins in the form of transparency, dimensional stability and molding processability.

BEST MODE FOR CARRYING OUT THE INVENTION

The following provides a detailed explanation of the present invention. Examples of polar substances present in a-methylstyrene to be removed by the purification method of the present invention may include carbonyl group-containing compounds, phenol and mixtures of catechols containing polymerization inhibitors in the form of t-butylcatechol. Specific examples of polar substances in the form of carbonyl group-containing compounds may include aliphatic carbonyl compounds in the form of compound represented by the following general formula (1) and aromatic carbonyl compounds in the form of compounds represented by the following general formula (2):

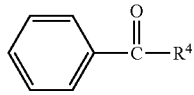
(2)

(wherein each of $R^1$, $R^3$ and $R^4$ independently represents a hydrogen atom or an alkyl group having 1 to 6 carbon atoms, and $R^2$ represents an alkyl group having 1 to 6 carbon atoms).

The term "alkyl group having 1 to 6 carbon atoms" used in the present specification refers to a linear or branched alkyl group having 1 to 6 carbon atoms, specific examples of which may include a methyl group, an ethyl group, a n-propyl group, an isopropyl group, a n-butyl group, an isobutyl group, a sec-butyl group, a tert-butyl group, a n-pentyl group, a 1,1-dimethylpropyl group, a 1,2-dimethylpropyl group, a 2,2-dimethylpropyl group, a 1-ethylpropyl group, a n-hexyl group, a 1-ethyl-2-methylpropyl group, a 1,1,2-trimethylpropyl group, a 1-ethylbutyl group, a 1-methylbutyl group, a 2-methylbutyl group, a 1,1-dimethylbutyl group, a 1,2-dimethylbutyl group, a 2,2-dimethylbutyl group, a 1,3-dimethylbutyl group, a 2,3-dimethylbutyl group, a 2-ethylbutyl group, a 2-methylpentyl group, a 3-methylpentyl group and the like. Preferable examples may include a methyl group, an ethyl group, a n-propyl group, an isopropyl group, a n-butyl group, an isobutyl group, a sec-butyl group, a tert-butyl group, a n-pentyl group, a n-hexyl group and the like.

In the present invention, more specific examples of the carbonyl group-containing compounds may include acetonylacetone, 3-methyl-2-cyclopentenone, benzaldehyde, acetophenone and the like. Since these polar substances inhibit polymerization or cause polymer coloring during production of poly-α-methylstyrene and copolymers thereof by anionic polymerization and the like, they are preferably removed as much as possible. Since polar substances other than water such as t-butylcatechol, acetonylacetone, 3-methyl-2-cyclopentenone, benzaldehyde and acetophenone have boiling points close to that of α-methylstyrene, they cannot be reduced beyond a certain level by the ordinary distillation.

The inventors of the present invention made it possible to remove trace amounts of these polar substances, which are unable to be removed by the ordinary distillation, by distillation by reacting in the presence of specific basic substances, and efficiently converting the polar substances that reacted in the presence of the basic substance to high boiling point compounds to increase the difference in relative volatility with that of α-methylstyrene. Moreover, the inventors of the present invention also found a method for obtaining highly pure α-methylstyrene by separating reaction products of the polar substance from α-methylstyrene and low boiling point components containing side reaction products, followed by further separating α-methylstyrene from the low boiling point components.

In the present invention, there are two possible reactions for obtaining high boiling point compounds by reacting the polar substances in the presence of a basic substance. The first method involves a reaction for obtaining a high boiling point compound by reacting phenol or catechols having an active hydrogen with base to form a salt, while the other method involves a reaction for increasing molecular weight by causing an aldehyde or ketone having one or more hydrogen atoms at the a position to undergo an intramolecular or intermolecular condensation reaction in the presence of a basic substance. In the case of the latter reaction in particular, since water or alcohol is produced by condensation as will be described to follow, and when considering that the reaction is an equilibrium reaction, it is extremely difficult to allow the reaction to proceed and increase molecular weight since the concentration of the reactants is extremely low.

In addition, although there are compounds that undergo an intermolecular reaction depending on the particular compound, in this case, since the boiling point is extremely close to that of the original polar substance, the compounds cannot be separated by distillation. The inventors of the present invention found that boiling point can be increased by converting these intermolecular condensation compounds to intermolecular compounds by treating under specific conditions.

Examples of aldehydes and ketones having a hydrogen atom at the α position may include acetonylacetone, 3-methyl-2-cyclopentenone and acetophenone. In the first stage, a basic substance removes the hydrogen atom at the α position resulting in the formation of an enolate and polar substance. Since this reaction is an equilibrium reaction and the equilibrium is generally biased toward the reactants side, it is difficult to form an enolate. Subsequently, in the second stage, the formed enolate undergoes an intermolecular addition reaction with the polar substance. As a result, since two or more polar substances increase in molecular weight and the difference in relative volatility with α-methylstyrene increases, they can be separated by distillation. A polar substance to which an enolate has been added may or may not have a hydrogen atom at the α position, and even benzaldehyde, which does not have a hydrogen atom at the α position, can be increased in molecular weight.

In particular, it is important in the present invention that the enolate formation of the first stage is carried out efficiently in order to carry out a condensation reaction at a trace concentration that generally proceeds with difficulty. Consequently, low boiling point by-products such as water and alcohol produced by the condensation reaction are discharged from the reaction system during the condensation reaction in the presence of a basic substance. As a result of discharging low boiling point by-products from the reaction system, the first stage equilibrium reaction is shifted toward the enolate formation side, thereby allowing the condensation reaction to proceed efficiently and making it possible to recover highly pure α-methylstyrene. Low boiling point by-products at this time indicate those having a boiling point lower than that of α-methylstyrene. Discharge of low boiling point by-products from the reaction system may be carried out continuously or sequentially within the reaction system.

The separation is only required to be that which separates low boiling point by-products from the reaction system, and typically consists of vaporizing the low boiling point by-products by heating the reaction system to a temperature equal to or higher than the boiling point of the low boiling point by-products in the manner of distillation. Examples of methods for discharging low boiling point by-products from the reaction system may include a method in which low boiling point by-products are separated from the reaction system, and the remaining α-methylstyrene and polar substance reaction product is separated by a method such as distillation; a method in which a mixture of α-methylstyrene and low boiling point by-products is discharged from the reaction system while at the same time separating the α-methylstyrene from the low boiling point by-products by distillation; and a method in which a mixture of α-methylstyrene and low boiling point by-products is separated from the reaction system followed by separating the α-methylstyrene and low boiling point by-products by distillation or adsorption using a column and the like. In the present invention, any of these methods may be used. What is important herein is that low boiling point by-products be efficiently removed from the reaction system, and that the condensation reaction be allowed to proceed efficiently as a result thereof.

There are no particular limitations on the basic substance used in the present invention provided it has basicity to a degree that enables it to remove a hydrogen atom at the α position of the polar substances. As an indicator of basicity, the pKa of the conjugate acid thereof is preferably 10 or more. Examples of basic substances that can be used may include those containing alkaline metals or alkaline earth metals including metal alkoxides such as sodium ethoxide, potassium ethoxide (conjugate acid: ethanol, pKa: 17) or sodium methoxide (conjugate acid: methanol, pKa: 16), metal hydroxides (conjugate acid:water, pKa: 16) such as sodium hydroxide, potassium hydroxide or magnesium hydroxide, metal oxides (conjugate acid:water, pKa: 16) such as sodium oxide, potassium oxide or magnesium oxide, metal amides such as sodium amide (conjugate acid: ammonia, pKa: 35) or lithium diisopropylamide (conjugate acid: diisopropylamine, pKa: 36), and alkyl metals such as butyl lithium (conjugate acid: butane, pKa: 45) or methyl lithium (conjugate acid: methane, pKa: 40).

These basic substances preferably have high solubility and dispersibility in α-methylstyrene. Although basic substances having high solubility and dispersibility in α-methylstyrene can be used as is, there are cases in which they are preferably used in the form of a solution by using a suitable solvent. In this case, there are no particular limitations on the solvent that composes the basic substance provided it has the ability to dissolve the basic substance, and water, alcohol or a mixed solution thereof, for example, can be used.

In this case, although water and alcohol inhibit the condensation reaction, following dispersion of a basic substance, this does not cause a problem provided that the water and alcohol are able to be discharged outside the reaction system along with low boiling point by-products. Thus, alcohols preferably have a boiling point at least lower than α-methylstyrene.

The concentration of the basic substance is preferably from 0.01 to 10% by weight and more preferably from 0.02 to 5% by weight based on α-methylstyrene. Although depending on the concentration of the basic substance, there are no particular limitations on the reaction time provided it is of a sufficient duration to allow the condensation reaction to proceed, and it is preferable to allow a certain amount of time for conversion to high boiling point intermolecular condensation products. Although reaction time is represented as the mean retention time in the case of a continuous reaction system or as the sum of the reaction time and distillation rate in the case of a batch reaction system, in the case of a basic substance at the concentrations indicated above, a preferable reaction time is at least 15 minutes, more preferably from 15 minutes to 4 hours and even more preferably from 30 minutes to 3 hours.

Any form of reaction system may be used in the present invention provided it allows the air-liquid equilibrium within the system to be substantially maintained. The operating pressure can be arbitrarily selected from within the range of atmospheric pressure to 5 kg/cm². In addition, there are also no particular problems even if the procedure is carried out under a reduced pressure. Although the temperature within the reaction system can be arbitrarily set according to the pressure, it is preferably from 40 to 200° C. and more preferably from 60 to 150° C. The ceiling temperature is 60° C. or higher in consideration of inhibiting polymerization of α-methylstyrene and 150° C. or lower in consideration of energy conservation of the heat source.

There are no particular limitations on the form in which α-methylstyrene and the basic substance are supplied provided low boiling point by-products such as water and alcohol produced by condensation can be sequentially removed, and they may be supplied by a batch operation or continuous operation.

The α-methylstyrene obtained according to the purification method of the present invention can be removed of impurities in the form of polar substances such as phenol, t-butylcatechol, acetonylacetone, 3-methyl-2-cyclopentenone or benzaldehyde and controlled to within a fixed range. Controlling these polar substances to within a fixed range is extremely effective for controlling polymerization and preventing polymer yellowing.

Although the lower the amount of polar substances the better, the total amount of acetonylacetone and its intramolecular condensation product in the form of 3-methyl-2-cyclopentenone is preferably 100 ppm by weight or less and more preferably 50 ppm by weight or less, and the amount of benzaldehyde is preferably 30 ppm by weight or less and more preferably 20 ppm by weight or less. If the total amount of acetonylacetone and its intramolecular condensation product in the form of 3-methyl-2-pentenone exceeds 100 ppm by weight or the amount of benzaldehyde exceeds 30 ppm by weight, yellowing of the resulting polymer becomes prominent, and living polymerization may be inhibited depending on the case.

The following provides a description of a styrene-based copolymer of a component that composes the heat-resistant styrene-based copolymer according to the present invention. A heat-resistant styrene-based copolymer in the present invention contains an α-methylstyrene unit, obtained by purification according to the purification method according to the present invention, and a vinyl aromatic unit. A copolymer containing a vinyl aromatic unit as referred to in the present invention is a copolymer obtained by polymerization using a vinyl aromatic monomer represented by the following formula (3) as a raw material:

(3)

(wherein $R^5$ represents a hydrogen atom, an alkyl group having 2 or more carbon atoms or a phenyl group, and $R^6$ represents a hydrogen atom, a halogen, a hydroxyl group, an alkyl group having 1 to 6 carbon atoms, an alkoxy group having 1 to 6 carbon atoms, a carboxyl group or a haloalkyl group having 1 to 6 carbon atoms).

The term "alkoxy group having 1 to 6 carbon atoms" used in the present specification refers to an oxy group to which is bonded a previously defined "alkyl group having 1 to 6 carbon atoms", specific examples of which may include a methoxy group, an ethoxy group, a n-propoxy group, an isopropoxy group, a n-butoxy group, an isobutoxy group, a sec-butoxy group, a tert-butoxy group, a n-pentyloxy group, an isopentyloxy group, a sec-pentyloxy group, a n-hexyloxy group, an isohexyloxy group, a 1,1-dimethylpropoxy group, a 1,2-dimethylpropoxy group, a 2,2-dimethylpropoxy group, a 2-methylbutoxy group, a 1-ethyl-2-methylpropoxy group, a 1,2,2-trimethylpropoxy group, a 1,1-dimethylbutoxy group, a 1,2-dimethylbutoxy group, a 2,2-dimethylbutoxy group, a 2,3-dimethylbutoxy group, a 1,3-dimethylbutoxy group, a 2-ethylbutoxy group, a 2-methylpentyloxy group, a 3-methylpentyloxy group and the like. Preferable examples may include a methoxy group, an ethoxy group, a n-propoxy group, an isopropoxy group and the like, and even more preferable examples may include a methoxy group and an ethoxy group.

The term "alkyl group having 2 or more carbon atoms" used in the present specification refers to a linear or branched alkyl group having 2 to 6 carbon atoms, specific examples of which may include an ethyl group, a n-propyl group, an isopropyl group, a n-butyl group, an isobutyl group, a sec-butyl group, a tert-butyl group, a n-pentyl group, a 1,1-dimethylpropyl group, a 1,2-dimethylpropyl group, a 2,2-dimethylpropyl group, a 1-ethylpropyl group, a n-hexyl group, a 1-ethyl-2-methylpropyl group, a 1,2,2-trimethylpropyl group, a 1-ethylbutyl group, a 1-methylbutyl group, a 2-methylbutyl group, a 1,1-dimethylbutyl group, a 1,2-dimethylbutyl group, a 2,2-dimethylbutyl group, a 1,3-dimethylbutyl group, a 2,3-dimethylbutyl group, a 2-ethylbutyl group, a 2-methylpentyl group, a 3-methylpentyl group and the like. Preferable examples may include an ethyl group, a n-propyl group, an isopropyl group, a n-butyl group, an isobutyl group, a sec-butyl group, a tert-butyl group, a n-pentyl group and the like.

The term "halogen atom" used in the present specification refers to a fluorine atom, a chlorine atom, a bromine atom or an iodine atom.

The term "haloalkyl group having 1 to 6 carbon atoms" used in the present specification refers to a group in which a previously defined "halogen atom" is bonded to a previously defined "alkyl group having 1 to 6 carbon atoms".

A vinyl aromatic monomer as used in the present description refers to, for example, styrene; an alkyl-substituted styrene such as p-methylstyrene, m-methylstyrene, o-methylstyrene, 2,4-dimethylstyrene, 2,5-dimethylstyrene, 3,4-dimethylstyrene, 3,5-dimethylstyrene, p-ethylstyrene, m-ethylstyrene or o-ethylstyrene; or other styrene derivative such as p-hydroxystyrene, p-methoxystyrene, p-chlorostyrene or 1,1-diphenylethylene. A preferable vinyl aromatic monomer is styrene. One type each of the α-methylstyrene and vinyl aromatic monomer may be used, or a mixture of two or more types may be used. In the present invention, the most preferable combination is the combination of styrene and α-methylstyrene obtained by purifying according to the purification method of the present invention.

The content of the α-methylstyrene unit in the styrene-based copolymer is from 5 to 70% by weight, preferably from 7 to 68% by weight and more preferably from 10 to 65% by weight. If the content of the α-methylstyrene unit is lower than 5% by weight, practical effects for improving heat resistance are virtually not observed. On the other hand, if the content of the α-methylstyrene unit exceeds 70% by weight, there is increased susceptibility to thermal decomposition during melting and molding while also increasing the amount of gas generated during molding. In addition, the amount of monomer components in the resin increase accompanying decomposition, thereby resulting in increased in the occurrence of bleedout on the surface of molded articles.

Other polymerizable monomers can be used in addition to the monomers described above within a range that does not impair the object of the present invention. Examples of other polymerizable monomers may include conjugated diene monomers such as butadiene or isoprene; methacrylic acid alkyl esters such as methyl methacrylate, ethyl methacrylate, propyl methacrylate or butyl methacrylate; and acrylic acid esters such as methyl acrylate, ethyl acrylate, propyl acrylate or butyl acrylate. These monomers are useful in the case of improving or adjusting impact strength, elongation or chemical resistance and the like of the resin.

The styrene-based copolymer in the present invention is synthesized by living anionic polymerization. A known method can be used to carry out living anionic polymerization. For example, an organic lithium compound is used for the initiator, specific examples of which may include n-butyl lithium, sec-butyl lithium, t-butyl lithium, ethyl lithium, benzyl lithium, 1,6-dilithiohexane, styryl lithium, butadienyl lithium and the like. Preferable examples may include n-butyl lithium and sec-butyl lithium.

A hydrocarbon-based compound not containing a hetero atom is preferable for the polymerization solvent, specific examples of which may include aliphatic hydrocarbon compounds such as n-hexane, cyclohexane or heptane, and aromatic hydrocarbon compounds such as benzene, toluene, ethylbenzene or xylene. One type or two or more types of these hydrocarbon compounds may be used. A particularly preferable compound is cyclohexane.

In addition, in the present invention, benzofuran may be added for the purpose of controlling polymerization. The inventors of the present invention found that the polymerization efficiency of α-methylstyrene can be improved dramatically by containing benzofuran in the living anionic polymerization system of the monomer containing α-methylstyrene.

In general, in styrene and conjugated diene living anionic polymerization systems, an ether compound such as tetrahydrofuran is known to be added for the purpose of improving the polymerization rate and promoting randomization during copolymerization. However, since tetrahydrofuran, for example, easily reacts with lithium compounds frequently used as initiators of living anionic polymerization systems depending on the polymerization temperature, there was the problem of decreasing initiator efficiency as a result of acting as an inhibitor.

On the other hand, the benzofuran used in the present invention contributes to increasing the polymerization rate and monomer reactivity without causing the above problems, and effectively acts to produce a heat-resistance styrene-based copolymer of a high molecular weight polymer. In the present invention, benzofuran is added to α-methylstyrene in an amount of from 5 to 5000 ppm, preferably from 10 to 4800 ppm and more preferably from 20 to 4500 ppm. If the added amount is lower than 5 ppm, the effect on the growing polymer species decreases. Namely, the effects on polymerization rate and polymerization conversion rate decrease thereby preventing the object of the present invention from being attained. Even if benzofuran is present in excess of 5000 ppm, no significant changes are observed in polymerization rate or conversion rate. In addition, since benzofuran is yellow in color, characteristic yellowing of the benzofuran becomes conspicuous during pelletization following removal of unreacted monomer and solvent, thereby making this undesirable depending on the application.

Benzofuran is not required to be added and mixed into the α-methylstyrene prior to polymerization, and may be mixed with other monomers and solvents.

The polymerization temperature is preferably within the range of from 40 to 110° C., more preferably within a range of from 50 to 100° C. and even more preferably within a range of from 55 to 95° C. If the polymerization temperature is lower than 40° C., the reaction rate decreases thereby making the process impractical for industrial production. In addition, if the polymerization temperature is higher than 110° C., yellowing of the copolymer becomes conspicuous while also causing decreases in weather resistance and thermal stability of the copolymer during melting.

The styrene-based copolymer according to the present invention can be produced by, for example, continuous living polymerization using a complex mixing type of polymerization reactor. Alternatively, a complete mixing type of polymerization reactor and non-complete mixing type of polymerization reactor may be combined. In order to obtain a random copolymer in particular, a complete mixing type of polymerization reactor is preferable. Complete mixing type polymerization refers to a method of polymerization that uses a continuous type of complete mixing reactor so that the concentrations of α-methylstyrene, vinyl aromatic monomer and living copolymer present in the living polymerization reaction system remain constant at all times.

In the case of desiring to enhance productivity by increasing the monomer concentration in the raw material solution, it is desirable to attach a condenser to the polymerization reactor and remove heat of polymerization with the latent heat of evaporation of a solvent to efficiently carry out removal of heat from the polymerization reaction. If mainly cyclohexane (which may also contain n-hexane) is used for the polymerization solvent in particular, it becomes easy to control the polymerization temperature in the vicinity of from 80 to 90° C. since the boiling point of cyclohexane is 82° C.

In the case of using a non-complete mixing type of tubular polymerization reactor, when it is difficult to obtain a completely mixed state within the polymerization reactor such as in the case the ratio (L/D) of the length (L) to the inner diameter (D) of the reactor is 1 or more or in the case of poor stirring efficiency, the styrene-based copolymer according to the present invention can be produced by adding a solution of vinyl aromatic monomer from a middle location in the reactor.

In addition, the copolymer of the present invention can also be obtained by connecting two or more non-complete mixing type of polymerization reactors in series and adding a solution of vinyl aromatic monomer to the second polymerization reactor followed polymerization in the first polymerization reactor. Moreover, a block copolymer of a homopolymer and copolymer of the vinyl aromatic unit can be obtained by only polymerizing the vinyl aromatic monomer unit in the first polymerization reactor and then carrying out copolymerization of α-methylstyrene and the vinyl aromatic monomer unit in the second polymerization reactor.

The value of the yellow index of the styrene-based copolymer according to the present invention is preferably 3 or less, more preferably 2 or less and even more preferably 1.5 or less. As was previously described, it is effective to reduce the content of polar substances in the α-methylstyrene purified by the purification method according to the present invention in order to lower the yellow index. During production of a biaxially oriented sheet (OPS) or foamed sheet (PSP) used in the field of food packaging in particular, there are cases in which yellowing of the resin becomes conspicuous causing problems in terms of quality as a result of recovering the sheet by winding. Thus, users of these types of applications are particularly sensitive to resin yellowing, thus making this an important performance requirement.

The ratio (Mz/Mw) of the Z-average molecular weight (Mz) to the weight average molecular weight (Mw) of the styrene-based copolymer containing α-methylstyrene purified by the purification method according to the present invention is within a range of from 1.4 to 3.0, preferably within a range of from 1.42 to 2.9 and even more preferably within a range of from 1.45 to 2.8. If the ratio of Mz/Mw is less than 1.4, the balance between fluidity and mechanical strength of the resin becomes poor resulting in the problem of making it difficult to increase the drawing ratio during biaxial orientation. In addition, if the ratio exceeds 3.0, the balance between fluidity and thermal decomposability becomes poor, thereby making it difficult to mold large molded articles, thin-walled molded articles and the like.

Examples of methods for controlling the value of Mz/Mw may include a method in which the range of molecular weight distribution is increased by carrying out polymerization in a reactor in which polymerization times are distributed; and a method in which two or more types of copolymers having different molecular weights are multiply dispersed by melting or solution blending. Z-average molecular weight (Mz) and weight average molecular weight (Mw) can be determined by converting to polystyrene using gel permeation chromatography (GPC).

Glass transition temperature in the present invention can be determined by DSC, and the temperature determined according to the method indicated in JIS-K7121 is used for the glass transition temperature.

Although there are no particular limitations on the bonding mode of the α-methylstyrene unit and vinyl aromatic monomer unit of the styrene-based copolymer according to the present invention, the most preferable bonding mode is a copolymer composed of random bonds. In general, susceptibility to thermal decomposition tends to increase the greater the number of chains of α-methylstyrene units present. Thus, depending on the application, it is preferable to control the number of chains of α-methylstyrene units to from 2 to 4 chains.

Since there is no risk of the vinyl aromatic units impairing thermal stability even if in the form of chains, they may be in the form of a long chain structure. The inventors of the present invention found that if vinyl aromatic units are of the AB type, in which long chains of vinyl aromatic units are present on the end of the molecular chain of the copolymer or in the form of block copolymers of the ABA type (wherein A represents a homopolymer component composed mainly of vinyl aromatic unit components, while B represents a random copolymer component containing α-methylstyrene units and vinyl aromatic units), other performance including heat resistance, thermal stability, mechanical properties and fluidity is equal to that of random copolymers, and that compatibility with homopolymers composed of the same structure as a component of the blocks in the form of the vinyl aromatic units is extremely favorable. In the case of reusing the styrene-based copolymer according to the present invention as a recycling material by taking advantage of this characteristic, such as in the case of reusing by melting and kneading with polystyrene, a copolymer can be used in which polystyrene chains are blocked on the ends of the polymer chains of the copolymer.

There are no particular limitations on the block chain length of the vinyl aromatic units, and the number average molecular weight of a block chain portion may be within a range of from 1000 to 300,000. In addition, the ratio of Mw/Mn of a block portion composed of vinyl aromatic units is preferably within a range of from 1.0 to 3.5.

The ratio of Mz/Mw of the Z-average molecular weight (Mz) to the weight average molecular weight (Mw) of a vinyl aromatic unit for the block component is required to be within a range of from 1.4 to 3.0, preferably within a range of from 1.42 to 2.9 and more preferably within a range of from 1.45 to 2.8. If the ratio of Mz/Mw is less than 1.4, the balance between fluidity and mechanical properties of the resin becomes poor, thereby making it difficult to demonstrate adequate performance as a resin molded article. In addition, if the ratio of Mz/Mw exceeds 3.0, fluidity becomes poor, thereby making it difficult to mold large molded articles, thin-walled molded articles and the like.

In a process for producing a copolymer having a vinyl aromatic unit for a block component, a homopolymer composed of vinyl aromatic units is produced with, for example, a batch-type reactor, a continuous tubular reactor, a continuous static mixer reactor, a continuous tank-type reactor with stirrer or a continuous coil-type reactor, followed by feeding α-methylstyrene, vinyl aromatic monomer and living homopolymer composed of vinyl aromatic units into a continuous complete mixing type of reactor and copolymerizing to obtain an AB type of block copolymer. In the case of obtaining an ABA type of block copolymer, vinyl aromatic units are subjected to living polymerization in a different reactor after having produced the AB type block copolymer. Alternatively, an ABA type of block copolymer can be obtained by adding a bifunctional compound that reacts with the growing living polymer species in a different reactor after having produced an AB type of living copolymer.

As a result of further conducting extensive studies, the inventors of the present invention found that a styrene-based copolymer composed of at least two types of copolymers containing an α-methylstyrene unit and vinyl aromatic unit obtained by continuous living polymerization, and in which the composite ratio in the copolymers obtained by supplying to a polymerization reactor differs as a result of continuously or intermittently changing the composite ratio of α-methylstyrene and vinyl aromatic monomer represented by the formula (3) in the raw materials, demonstrates other performance including heat resistance, thermal stability, mechanical properties and fluidity equal to that of random copolymers, and compatibility with copolymers having a vinyl aromatic component as a main component thereof is extremely favorable.

This suggests that, in the case of recycling molded articles of this copolymer, polymers composed mainly of vinyl aromatic units such as polystyrene can also be reused as recycling materials by blending. Different copolymers refer to copolymers in which the glass transition temperature thereof differs by at least 3° C.

The supplying to a polymerization reactor by continuously or intermittently changing the composite ratio of α-methylstyrene and vinyl aromatic monomer among the monomers means that the concentration of each monomer introduced into the polymerization reaction system changes either continuously or intermittently, and as a result, the composite ratio of each aromatic unit of the resulting copolymer changes resulting in the sequential acquisition of copolymers composed of at least two different composite ratios.

Copolymers having two or more different composite ratios may be mixed in a solution state in a batch-type tank followed by flushing into a tank heated in a vacuum to remove the solvent, or can be recovered in the form of pellets by removing the solvent using an extruder or kneader. Alternatively, they can also be recovered in the form of pellets directly without retaining in batch-type tank, and the pellets can then be mixed and made uniform in a batch-type or continuous mixing vessel. Alternatively, after putting the pellets into a uniform state in a mixing vessel, the pellets can be further melted and mixed using an extruder.

As a specific production example, after feeding a raw material having a composite ratio M1/M2 of α-methylstyrene (M1) to vinyl aromatic monomer (M2) of 50/50 (wt %) into a reactor and polymerizing, feeding is switched over to a raw material having a different composite ratio, such as M1/M2 of 40/60 (wt %) which is also introduced into the reactor followed by carrying out polymerization. In this case, the raw material composition is said to change intermittently. When polymerized in this manner, copolymers are sequentially obtained having compositions that continuously change from the composition of the copolymer obtained by polymerizing at an M1/M2 ratio of 50/50 (wt %) to the composition of the copolymer obtained by polymerizing at an M1/M2 ratio of 40/60 (wt %). The resulting copolymers are then mixed in solution or stirred and mixed in the form of pellets in a batch-type reactor followed by melting and kneading to obtain a copolymer having a certain fixed composition.

Copolymers obtained according to such a method can be considered to have a copolymer composition in which the composite ratios of the α-methylstyrene unit and vinyl aromatic unit components differ. Copolymers obtained as a result thereof have extremely good compatibility with homopolymers of vinyl aromatic monomers, and since they are able to maintain transparency without causing a decrease in mechanical properties, they were determined to be polymers having extremely high utilization value as recycling materials.

In the living anionic polymerization serving as the production process of the copolymer of the present invention, completion of the polymerization reaction is preferably carried out in the case the reactivity of the vinyl aromatic monomer has reached 99% or more, and α-methylstyrene may remain in the reaction system. Termination of the polymerization reaction is carried out by addition of a reaction terminator in the form of a compound having an oxygen-hydrogen bond such as water, alcohol, phenol or carboxylic acid, and similar effects can also be expected for epoxy compounds, ester compounds, ketone compounds, carboxylic acid anhydrides and compounds having a carbon-halogen bond. The amount of these additives used is preferably about one to ten equivalents of the growing species. If the amount of these additives used is excessively large, not only is this disadvantageous in terms of costs, but there are many cases in which it impairs mixing of remaining additives.

Polymer molecular weight can be increased and the polymer chain can be made to have a branched structure by carrying out a coupling reaction with a multifunctional compound using the growing living polymer species. A known compound can be selected for the multifunctional compound used in this type of coupling reaction. Examples of multifunctional compounds may include polyhalogen compounds, polyepoxy compounds, mono- or polycarboxylic acid esters, polyketone compounds, mono- or polycarboxylic acid anhydrides and the like. Specific examples may include silicon tetrachloride, di(trichlorosilyl)ethane, 1,3,5-tribromobenzene, epoxidated soybean oil, tetraglycidyl 1,3-bisaminomethylcyclohexane, dimethyl oxalate, tri-2-ethylhexyl trimellitate, pyromellitic dianhydride, diethyl carbonate and the like.

Following completion of polymerization, unreacted monomer and solvent are removed by volatilization from the polymer for recovery and regeneration. A known method can be used for volatilization removal. A method involving flushing into a vacuum tank and/or a method involving heating to evaporation in a vacuum using an extruder or kneader can be preferably used for the volatilization removal apparatus. Although varying according to the volatility of the solvent, volatile components such as solvent and residual monomers are typically removed by volatilization at a temperature of from 180 to 300° C. and degree of vacuum of from 100 Pa to 50 KPa.

A method in which volatilization removal apparatuses are connected in series and arranged in two or more stages is also effective. In addition, a method can also be used in which water is added between the first stage and second stage to enhance the ability of the second stage to volatilize monomer. Moreover, after removing volatile components with a flushing tank, an extruder provided with a vent can be used to remove residual volatile components. The styrene-based copolymer that has been removed of solvent can be finished into pellets using a known method.

Known compounds used in styrene-based resins can be added to the styrene-based copolymer according to the present invention for the purpose of improving thermal and mechanical stability, fluidity and coloring as necessary. Examples of such additives may include primary antioxidants in the form of 2,4,6-tri-substituted phenols such as 2,6-di-t-butyl-4-methylphenol, triethylene glycol-bis-[3-(3-t-butyl-5-methyl-4-hydroxyphenyl)propionate], pentaerythritol tetraquis[-(3,5-di-t-butyl-4-hydroxyphenyl) propionate], octadecyl-3-(3,5-di-t-butyl-4-hydroxyphenyl)propionate, 1,3,5-trimethyl-2,4,6-tris(3,5, -di-t-butyl-4-hydroxybenzyl) benzene, n-octadecyl-3-(3,5-di-t-butyl-4-hydroxyphenyl) propionate, 2-t-butyl-6-(3-t-butyl-2-hydroxy-5-methylbenzyl)-4-methylphenyl acrylate, 2[1-(2-hydroxy-3,5-di-t-pentylphenyl)]-4,6-di-t-pentyl phenyl acrylate, tetraquis [methylene-3-(3,5-di-t-butyl-4-hydroxyphenyl)propionate] methane, 3,9-bis[2-{3-(t-butyl-4-hydroxy-5-methylphenyl) propionyloxy}-1,1-dimethylethyl]-2,4,8,10-tetraoxa[5,5] undecane, 1,3,5-tris(3',5'-di-t-butyl-4'-hydroxybenzyl)-s-triazine-2,4,6(1H ,2H, 3H )-trione, 1,1,4-tris(2-methyl-4-hydroxy-5-t-butylphenyl) butane, 4,4'-butylidenebis(3-methyl-6-t-butylphenol) and the like.

In addition, phosphorous-based antioxidants or sulfur-based antioxidants can be added as secondary antioxidants, and hindered amine stabilizers or UV absorbers can be added as weather resistance agents. In addition, plasticizers such as mineral oils, lubricants such as long-chain aliphatic carboxylic acids and/or metal salts thereof, coloring improvers such as organic dyes or organic pigments can also be added.

Anthraquinone-based organic dyes for improving coloring are particularly preferable because of little impairment of thermal stability of the copolymer.

Silicone-based and fluorine-based mold release agents, antistatic agents and other known technologies used in styrene-based resins can also be applied directly.

These stabilizers can be added and mixed into a polymer solution following completion of polymerization, or they can be melted and mixed using an extruder following recovery of polymer.

The styrene-based copolymer according to the present invention is preferably suitable for injection molded articles. In particular, it can be used in structural materials and containers requiring transparency, heat resistance and high rigidity, as well as in molded articles and electric lighting covers requiring weather resistance.

EXAMPLES

The following provides a more detailed explanation of the distillative purification conditions of the present invention through examples thereof. Furthermore, the present invention is not limited by these examples.

First, the following provides a description of evaluation methods used in the examples and comparative examples.

<Evaluation Methods>

(1) Solubility of Basic Substances in α-Methylstyrene

The solubility of basic substances in α-methylstyrene was judged visually and evaluated based on the following criteria. In the case a basic substance is a solution, the state of α-methylstyrene in the reaction oven was observed after recovering the solvent of the basic substance in the form of an initial fraction.

◯: Uniformly dissolved and transparent.
Δ: Slightly dispersed or suspended.
x: Completely separated.

(2) α-Methylstyrene Purification Effects

Polar substances contained in the recovered main fraction were quantified by gas chromatography (GC-14A, Shimadzu Corp.). The amount of polar substances was taken to be the total amount of acetonylacetone, 3-methyl-2-cyclopetenone, benzaldehyde and acetophenone. The polar substance removal rate was determined based on the following formula 1.

Removal rate (%)=Amount of reduction in polar substances (ppm)/Content of polar substances before purification (ppm)×100

◉: Removal rate of greater than 99%.
◯: Removal rate of greater than 90% to 99%.
Δ: Removal rate of greater than 80% to 90%.
X: Removal rate of 80% or lower.

<Production Process>

Production Example 1

(1) Raw Materials

After storing styrene (St: Sumitomo Chemical Co., Ltd.) and cyclohexane (CH: Idemitsu Petrochemical Co., Ltd.) in a storage tank and bubbling with nitrogen, the solution was passed through a purification column packed with activated alumina (KHD-24, Sumika Alchem Co., Ltd.) having a volume of 5 liters to remove polymerization inhibitor in the form of t-butylcatechol.

α-Methylstyrene (αMeSt: Mitsui Chemicals, Inc.) was purified under the conditions indicated in the subsequently described examples and comparative examples.

(2) Initiator n-Butyl lithium (15 wt % n-hexane solution, Wako Pure Chemical Industries, Ltd.) was diluted with cyclohexane by a factor of 1/61.

(3) Terminator

Methanol (analytical grade, Wako Pure Chemical Industries, Ltd.) was diluted with cyclohexane to a concentration of 3 wt %.

(4) Polymerization Method

A jacketed 5-liter reactor (R1) attached with a stirrer (Maxblend Impeller, Sumitomo Heavy Industries, Ltd.) and condenser and further equipped with a raw material feed nozzle, initiator feed nozzle and polymerization solution discharge nozzle was used for the polymerization reactor. The outlet of the condenser was sealed with nitrogen gas to prevent entrance of outside air. The volume of polymerization solution in the polymerization reactor was controlled to 3 liters at all times. A portion of the polymerization solution was continuously maintained in a boiling state and internal temperature was controlled to from 82 to 84° C. The rotating speed of the stirrer was 320 rpm. Gear pumps were respectively attached to the raw material inlet and outlet of the polymerization reactor, and the polymerization solution was controlled so that a solution mixed at a ratio of St/αMeSt/CH of Oct. 21, 1969 (wt %) was allowed to flow at a constant flow rate of 1.5 L/Hr. In addition, the initiator was introduced into the polymerization reactor at 0.07 L/Hr.

The living polymer solution discharged from the polymerization reactor was further led to the inlet of the polymerization terminator solution through a pipe having a diameter of 10 mm with a gear pump. The length of pipe from the reactor to the location of mixing with the polymerization terminator was about 2 m, and the pipe was maintained at a temperature of 65 to 70° C. The terminator solution was introduced into the polymerization reaction solution at a flow rate of 0.1 L/Hr, and subsequently terminated the polymerization reaction after passing through a static mixer having a volume of 1.2 liters (Model SMX, Sulzer Corp.). Moreover, the polymer solution was heated to 260° C. with a preheater and then flushed into an approximately 50 L reactor heated to a set temperature of 260° C. under a reduced pressure of 60 torr followed by separation and recovery of solvent and unreacted monomer from the polymer. The temperature of the polymer in the flushing container was about 240 to 250° C., and the retention time of the polymer in the tank was about 20 to 30 minutes. After being adequate removed of volatile components, the polymer was subsequently discharged in the form of a rope, cooled with water and then palletized with a cutter to recover styrene-based copolymer.

Production Example 2

A styrene-based copolymer was obtained by polymerizing under the same conditions and using the same method as Production Example 1 with the exception making the flow rate of initiator solution into the polymerization reactor 0.16 L/Hr.

<Analytical Methods>

(1) Measurement of Molecular Weight (Mn, Mw, Mz, Mz/Mw)

Molecular weights were measured with a GPC system consisting of connecting two columns (TSKgel SuperHZM-H, 40° C.) to the HLC-8220 manufactured by Toray Industries, Inc. and provided with an RI detector. THF was used for the mobile phase. Calculation of molecular weights was carried out by preparing calibration curves using polystyrene standards (Toray Industries, Inc.) and then converting as polystyrene.

(2) Measurement of Polymerization Rates

Samples of polymer solution were collected after terminating polymerization followed by quantification of the amounts of styrene monomer and α-methylstyrene remaining in the solution by gas chromatography (GC-14B, Shimadzu Corp.). Each polymerization rate was determined based on formula (a) below.

Polymerization rate (%)=(1−(monomer concentration remaining in polymer solution after polymerization/monomer concentration in raw material solution before polymerization))×100   Formula (a)

<Molding Method>

Molding was carried out under the following conditions using an injection molding machine manufactured by Funac, Ltd. (AUTO SHOT 15A). The cylinder temperatures were set to be 215° C., 225° C., 230° C. and 230° C. moving from the hopper side. The mold temperature was set to be 60° C., injection time to be 10 seconds and cooling time to be 20 seconds. Molten resin was filled by applying pressure 5 MPa higher than the injection pressure at which resin is filled into the mold. An ASTM No. 4 dumbbell having a thickness of 3 mm was molded and used as the sample for measurement of yellow index.

<Evaluation Methods>

(1) Evaluation of Polar Substance Content of x-Methylstyrene

Polar substances contained in sampled α-methylstyrene were quantified by gas chromatography (GC-1700, Shimadzu Corp.). The temperature of the column (HR-20, manufactured by Shinwa Chemical Industries, Ltd.) was held at 110° C. for 10 minutes and then raised to 160° C. at the rate of 5° C./min and then further raised to 230° C. at the rate of 5° C./min followed by measurement.

(2) Evaluation of Dimer Content of α-Methylstyrene

Polar substances contained in the sampled α-methylstyrene were quantified by gas chromatography (GC-1700, Shimadzu Corp.). Measurement was carried out under the following conditions.

Column: HR-1 (0.32 mm×30 m×0.25 μm), non-polar

Carrier gas: He (1 ml/min, split ratio: 1:10)

Column temperature: 200° C.→(3° C./min)→290° C. (40° C./min)→300° C. (held for 20 minutes)

Sample injection port temperature: 250° C.

Detector temperature: 280° C.

(3) Evaluation of Living Index

Living index is an indicator that expresses the closeness to ideal living polymerization. In the case of ideal living polymerization, since the concentration of the active species does not change before and after polymerization, the number average molecular weight (Mn) as calculated from the resulting polymer is represented with the following formula (b).

Ideal Mn=Weight of all reacted monomers (g)/total amount of initiator (mol)   Formula (b)

The living index is taken to be the difference between the above ideal Mn and the Mn of the polymer actually obtained, is determined based on the following formula (c), and is defined as indicated below.

Living index=Ideal Mn/Mn of resulting polymer   Formula (c)

○: Living index of greater than 0.8 to 1.2.

Δ: Living index of greater than 0.7 to 0.8 or greater than 1.2 to 1.3.

X: Living index of 0.7 or less or greater than 1.3.

(4) Glass Transition Temperature (Tg)

Glass transition temperature (Tg) was determined in compliance with JIS-K-7121 using the DSC-7 manufactured by Perkin-Elmer Corp. More specifically, the temperature was raised to 250° C. at the rate of 10° C./min, returned to room temperature at the rate of 10° C./min and again raised to 250° C. at the rate of 1° C./min in the presence of nitrogen. The glass transition temperature measured during the course of the second temperature rise was used as the value of Tg.

(5) Yellow Index

Yellow index was measured in accordance with JIS-K7103 using the SM-5-CH—H2 manufactured by Suga Test Instruments Co., Ltd.

◉: Yellow index of 1.5 or lower.

○: Yellow index of greater than 1.5 to 2.0.

Δ: Yellow index of greater than 2.0 to 3.0.
X: Yellow index of 3.0 or more.

Example 1

Distillation was carried out by simple distillation. More specifically, a thermometer for measuring liquid temperature was attached to a 300 ml reaction flask containing a rotor, and a K-tube attached with a thermometer for measuring water vapor temperature, a Liebig condenser, a two-way adapter and a holding flask were attached thereto. Moreover, a vacuum pump was connected to the adapter through a vacuum controller (VC-30S, Okano Works, Ltd.) to enable adjustment of the degree of decompression. An oil bath was used for the heat source.

200 ml of α-methylstyrene (Mitsui Chemicals, Inc.) were placed in the reaction flask and the liquid temperature was raised to be 80° C. Subsequently, a basic substance in the form of 0.08% by weight of sodium ethoxide (20% by weight ethanol solution, Wako Pure Chemical Industries, Ltd.) was added to the reaction flask while stirring with the rotor. The degree of decompression was adjusted to 230 mmHg and the liquid temperature was slowly raised to be from 120 to 125° C.

A low boiling point fraction that condensed after reached a boiling point during heating was recovered as an initial fraction.

The main fraction was recovered when the liquid temperature reached 120 to 125° C. and the water vapor temperature also reached 120 to 125° C. The contents of phenol and t-butylcatechol in the purified α-methylstyrene were below the detection limit (2 ppm by weight).

Example 2

Example 2 was carried out in the same manner as Example 1 with the exception of making the added amount of sodium ethoxide (20% by weight ethanol solution, Wako Pure Chemical Industries, Ltd.) 0.4% by weight. The contents of phenol and t-butylcatechol in the purified α-methylstyrene were below the detection limit (2 ppm by weight).

Example 3

A thermometer for measuring liquid temperature was attached to a 160 ml 5-mouth reaction flask containing a rotor, and a K-tube attached with a thermometer for measuring water vapor temperature, a Liebig condenser, a two-way adapter and a holding flask were attached thereto. Moreover, a vacuum pump was connected to the adapter through a vacuum controller (VC-30S, Okano Works, Ltd.) to enable adjustment of the degree of decompression. Moreover, α-methylstyrene was fed into the flask at the rate of 1.99 ml/min through a pump A. In addition, sodium ethoxide (20% by weight ethanol solution, Wako Pure Chemical Industries, Ltd.) was fed into the flask at the rate of 0.008 ml/min through a microfeeder (pump B). The liquid inside the flask was discharged at the rate of 0.1 ml/min using a pump C. The pressure inside the system was maintained at 230 mmHg and distillation was carried out at the rate of 1.9 ml/min. An oil bath was used for the heat source. Once conditions had stabilized, the distilled monomer liquid was analyzed. The contents of phenol and t-butylcatechol in the purified α-methylstyrene were below the detection limit (2 ppm by weight).

Example 4

Example 4 was carried out in the same manner as Example 2 with the exception of using sodium hydroxide (50% by weight aqueous solution, Wako Pure Chemical Industries, Ltd.) for the basic substance.

Example 5

Purification of α-methylstyrene was carried out by adding 0.8% by weight of a basic substance in the form of sodium ethoxide (20% by weight ethanol solution, Wako Pure Chemical Industries, Ltd.), distilling at a degree of decompression of 230 mmHg and liquid temperature of from 120 to 125° C., and recovering the main fraction when the water vapor temperature reached 120 to 125° C. The contents of phenol and t-butylcatechol in the purified α-methylstyrene were below the detection limit (2 ppm by weight). Production of styrene-based resin copolymer was carried out according to the process described in Production Example 1.

The number average molecular weight Mn of the resulting styrene-based copolymer was 98,000. In addition, the polymerization rates were 99.7% for St and 48.9% for α-MeSt.

Example 6

Purification of α-methylstyrene was carried out in the same manner as Example 1. The contents of phenol and t-butylcatechol in the purified α-methylstyrene were below the detection limit (2 ppm by weight). Production of styrene-based copolymer was carried out according to the process described in Production Example 2.

The number average molecular weight Mn of the resulting styrene-based copolymer was 62,000, and the polymerization rates were 99.8% for St and 47.5% for α-MeSt.

Example 7

Purification of α-methylstyrene was carried out in the same manner as Example 2. The contents of phenol and t-butylcatechol in the purified α-methylstyrene were below the detection limit (2 ppm by weight). Production of styrene-based copolymer was carried out according to the process described in Production Example 2.

The number average molecular weight Mn of the resulting styrene-based copolymer was 61,000, and the polymerization rates were 99.7% for St and 46.5% for α-MeSt.

Example 8

Purification of α-methylstyrene was carried out in the same manner as Example 3. The contents of phenol and t-butylcatechol in the purified α-methylstyrene were below the detection limit (2 ppm by weight). Production of styrene-based copolymer was carried out according to the process described in Production Example 2.

The number average molecular weight Mn of the resulting styrene-based copolymer was 60,000, and the polymerization rates were 99.6% for St and 46.3% for α-MeSt.

Example 9

Purification of α-methylstyrene was carried out in the same manner as Example 3. The contents of phenol and t-butylcatechol in the purified α-methylstyrene were below the detection limit (2 ppm by weight). Production of styrene-based copolymer was carried out according to the process described in Production Example 2.

The number average molecular weight Mn of the resulting styrene-based copolymer was 61,000, and the polymerization rates were 99.7% for St and 46.4% for α-MeSt.

Reference Example 1

Polymerization was carried out in accordance with Production Example 2 by adding benzofuran to the polymerization raw material solution (mixed solution of styrene, α-methylstyrene and cyclohexane) to a concentration of 65 ppm based on the α-methylstyrene.

Reference Examples 2 to 7

Benzofuran in the amounts shown in Table 3 was added to the polymerization raw material solution. Other conditions were the same as in Example 10.

Comparative Example 1

Reference Example 1 was carried out in the same manner as Example 2 with the exception of using diethanolamine (analytical grade, Wako Pure Chemical industries, Ltd.) for the basic substance.

Comparative Example 2

Reference Example 2 was carried out in the same manner as Example 2 with the exception of using pyridine (analytical grade, Wako Pure Chemical Industries, Ltd.) for the basic substance.

Comparative Example 3

200 ml of α-methylstyrene (Mitsui Chemicals, Inc.) were placed in a 300 ml separatory funnel followed by the addition of 50 ml of sodium hydroxide (10% by weight aqueous solution, Wako Pure Chemical Industries, Ltd.) and shaking 100 times. After allowing to stand undisturbed, a procedure for removing only the aqueous layer was repeated five times. Subsequently, 50 ml of distilled water were added instead of aqueous sodium hydroxide solution and the same procedure was repeated until the aqueous layer became neutral. The oily layer was then removed and a distillation procedure was carried out in the same manner as Example 2 without adding a basic substance.

Comparative Example 4

A distillation procedure was carried out in the same manner as Example 2 without adding a basic substance.

Comparative Example 5

Purification of α-methylstyrene was carried out by storing the α-methylstyrene in a storage tank and bubbling with nitrogen followed by passing through a purification column having an inner diameter of 76.3 mm, height of 600 mm and volume of 2.5 liters packed with activated alumina (KHD-24, Sumika Alchem Co., Ltd.).

The contents of basic substances in the a-methylstyrene were measured by sampling α-methylstyrene that eluted from a purification column 200 hours after the start of passage of α-methylstyrene through the purification column.

Production of styrene-based copolymer was carried out using the method described in Production Example 2 with the exception of using α-methylstyrene sampled 200 hours after the start of passage of α-methylstyrene through the purification column.

The number average molecular weight Mn of the resulting styrene-based copolymer was 61,000, and the polymerization rates were 99.5% for St and 46.2% for α-MeSt.

Comparative Example 6

Purification of α-methylstyrene was carried out in the same manner as

Comparative Example 5.

The content of polar substances in the α-methylstyrene was measured by sampling α-methylstyrene that eluted from a purification column 300 hours after the start of passage of α-methylstyrene through the purification column.

Production of styrene-based copolymer was carried out using the method described in Production Example 2 with the exception of using α-methylstyrene sampled 300 hours after the start of passage of α-methylstyrene through the purification column.

The number average molecular weight Mn of the resulting styrene-based copolymer was 60,000, and the polymerization rates were 80.8% for St and 5.7% for α- MeSt.

Reference Examples 6 and 7

Benzofuran was added to the polymerization raw material solution in the amounts shown in Table 3. Other conditions were the same as in Example 10.

<Evaluation Results>

The results of evaluating the examples and comparative examples are shown in Table 1.

TABLE 1

| | Example 1 | Example 2 | Example 3 | Example 4 |
|---|---|---|---|---|
| Basic substance | NaOEt EtOH sol. | NaOEt EtOH sol. | NaOEt EtOH sol. | NaOH $H_2O$ sol. |
| pKa of conjugated acid | 17 | 17 | 17 | 16 |
| Catalyst concentration | 0.08 | 0.4 | 0.08 | 0.4 |
| Discharge of low molecular weight by-products | Yes | Yes | Yes | Yes |
| Solubility | ○ | ○ | ○ | Δ |
| Purification effects | ○ | ◎ | ○ | Δ |

| | Comp. Example 1 | Comp. Example 2 | Comp. Example 3 | Comp. Example 4 |
|---|---|---|---|---|
| Basic substance | $(EtOH)_2NH$ | Pyridine | NaOH $H_2O$ sol. | None |
| pKa of conjugated acid | 9 | 6 | 16 | — |
| Catalyst concentration | 0.4 | 0.4 | — | 0 |
| Discharge of low molecular weight by-products | Yes | Yes | No | — |
| Solubility | Δ | ○ | — | — |
| Purification effects | X | X | X | X |

TABLE 2

| | | Basic Substance Content in α-methylstyrene | | Styrene-based Copolymer Evaluation Results | | |
|---|---|---|---|---|---|---|
| | Production Process | Acetonylacetone and 3-methyl-2-cyclopentenone (wt ppm) | Benzaldehyde (wt ppm) | Living index | Glass transition temperature Tg (°C.) | Yellow index YI |
| Example 5 | Production Example 1 | <2 | <2 | ○ | 131 | ◎ |
| Example 6 | Production Example 2 | <2 | <2 | ○ | 131 | ◎ |
| Example 7 | Production Example 2 | <2 | <2 | ○ | 130 | ◎ |
| Example 8 | Production Example 2 | 36 | 15 | ○ | 130 | ○ |
| Example 9 | Production Example 2 | 72 | 21 | ○ | 130 | ◎ |
| Comparative Example 5 | Production Example 2 | 105 | 32 | ○ | 130 | X |
| Comparative Example 6 | Production Example 2 | 185 | 52 | X | 106 | X |

TABLE 3

| | Amount of benzofuran added to α-methylstyrene (ppm) | Conv. Styrene | Conv. α-MeSt | Molecular Weight Mw × 10$^{-4}$ | Molecular Weight Mn × 10$^{-4}$ | DSC Tg | Yellow Index (YI) |
|---|---|---|---|---|---|---|---|
| Reference Example 1 | 65 | >99.9 | 50 | 23.8 | 11.3 | 125 | ○ |
| Reference Example 2 | 210 | >99.9 | 65 | 26.3 | 12.5 | 131 | ○ |
| Reference Example 3 | 500 | >99.9 | 72 | 28.7 | 14 | 133 | ○ |
| Reference Example 4 | 1000 | >99.9 | 75 | 28.7 | 14 | 134 | ◎ |
| Reference Example 5 | 4000 | >99.9 | 76 | 28.7 | 14.1 | 134 | ◎ |
| Reference Example 6 | 10000 | >99.9 | 74 | 28.5 | 13.8 | 134 | X |
| Reference Example 7 | 0 | >99.9 | 44 | 21.2 | 10.2 | 121 | ○ |

INDUSTRIAL APPLICABILITY

According to the present invention, highly pure α-methylstyrene can be provided by efficiently removing trace amounts of polar substances contained in α-methylstyrene, which were unable to be removed in the prior art, without requiring a complex process. The resulting α-methylstyrene is useful as a monomer for industrial production of polymers, and allows the obtaining of high molecular weight polymers free of coloring.

The invention claimed is:

1. A method for producing α-methylstyrene, comprising the steps of:
    reacting a polar substance which contains a carbonyl-containing compound, and which is contained in α-methylstyrene in the presence of a basic substance wherein a basicity of the basic substance is 10 or more in terms of an acid dissociation constant pKa of a conjugate acid of the basic substance;
    separating a low boiling point component produced by the reaction from a mixture of a reaction product of the polar substance containing the carbonyl-containing compound and α-methylstyrene; and
    separating α-methylstyrene from the mixture of the reaction product of the polar substance containing the carbonyl-containing compound and α-methylstyrene.

2. A method for producing α-methylstyrene, comprising the steps of:
    reacting a polar substance which contains a carbonyl-containing compound, and which is contained in α-methylstyrene in the presence of a basic substance wherein a basicity of the basic substance is 10 or more in terms of an acid dissociation constant pKa of a conjugate acid of the basic substance;
    separating a mixture of a low boiling point component produced by the reaction and α-methylstyrene from a reaction product of the polar substance containing the carbonyl-containing compound and α-methylstyrene; and
    separating α-methylstyrene from the mixture of the reaction product of the polar substance containing the carbonyl-containing compound and α-methylstyrene.

3. The method for producing α-methylstyrene according to claim 1 or 2, wherein the basic substance is a basic compound containing an alkaline metal or alkaline earth metal.

4. The method for producing α-methylstyrene according to claim 1 or 2, wherein the polar substance containing the carbonyl-containing compound contains a carbonyl group-containing compound and a mixture of phenol and catechol.

5. The method for producing α-methylstyrene according to claim 4, wherein the carbonyl group-containing compound is a compound represented by the following general formula (1) or general formula (2):

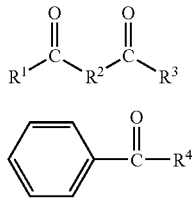
(1)

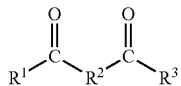
(2)

(wherein each of $R^1$, $R^3$ and $R^4$ independently represents a hydrogen atom or an alkyl group having 1 to 6 carbon atoms, and $R^2$ represents an alkyl group having 1 to 6 carbon atoms).

6. The method for producing α-methylstyrene according to claim 5, wherein the carbonyl group-containing compound contains at least one compound selected from acetonylacetone, 3-methyl-2-cyclopetenone, benzaldehyde and acetophenone.

7. A method for producing a styrene-based copolymer by living anionic polymerization using α-methylstyrene for anionic polymerization, wherein a total content of an aliphatic carbonyl compound represented by the following general formula (1) and an intramolecular dehydration condensate thereof is 100 ppm by weight or less, and a content of an aromatic carbonyl compound represented by the following general formula (2) is present at 30 ppm by weight or less:

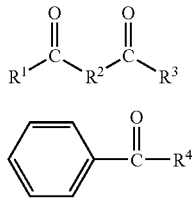
(1)

-continued

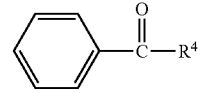
(2)

(wherein each of $R^1$, $R^3$ and $R^4$ independently represents a hydrogen atom or an alkyl group having 1 to 6 carbon atoms, and $R^2$ represents an alkyl group having 1 to 6 carbon atoms).

8. The method for producing a styrene-based copolymer according to claim 7, wherein a content of alcohol, phenol and catechols contained in the α-methylstyrene is 10 ppm by weight or less.

9. The method for producing a styrene-based copolymer according to claim 7 or 8, wherein a content of α-methylstyrene dimer contained in the α-methylstyrene is less than 5 ppm by weight.

10. The method for producing a styrene-based copolymer according to claim 7 or 8, wherein the living anionic polymerization is carried out by using the α-methylstyrene and a vinyl aromatic monomer represented by the following general formula (3):

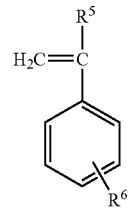
(3)

(wherein $R^5$ represents a hydrogen atom, an alkyl group having 2 or more carbon atoms or a phenyl group, and $R^6$ represents a hydrogen atom, a halogen, a hydroxyl group, an alkyl group, an alkoxy group, a carboxyl group or a haloalkyl group).

* * * * *